(12) United States Patent
Zhang et al.

(10) Patent No.: US 10,796,221 B2
(45) Date of Patent: Oct. 6, 2020

(54) DEEP LEARNING ARCHITECTURE FOR AUTOMATED IMAGE FEATURE EXTRACTION

(71) Applicant: General Electric Company, Schenectady, NY (US)

(72) Inventors: Min Zhang, San Ramon, CA (US); Gopal Biligeri Avinash, San Ramon, CA (US)

(73) Assignee: General Electric Company, Schenectady, NY (US)

( * ) Notice: Subject to any disclaimer, the term of this patent is extended or adjusted under 35 U.S.C. 154(b) by 93 days.

(21) Appl. No.: 15/854,971

(22) Filed: Dec. 27, 2017

(65) Prior Publication Data
US 2019/0122074 A1 Apr. 25, 2019

Related U.S. Application Data

(60) Provisional application No. 62/574,333, filed on Oct. 19, 2017.

(51) Int. Cl.
*G06K 9/00* (2006.01)
*G06N 3/04* (2006.01)
(Continued)

(52) U.S. Cl.
CPC ......... *G06N 3/0454* (2013.01); *G06K 9/6267* (2013.01); *G06N 3/08* (2013.01);
(Continued)

(58) Field of Classification Search
CPC ....... G06T 7/0016; G06T 3/4046; G06T 5/20; G06T 7/0012; G06T 2207/10024;
(Continued)

(56) References Cited

U.S. PATENT DOCUMENTS 5,769,074 A 6/1998 Barnhill et al.
8,064,660 B2 11/2011 Leow et al.
(Continued)

FOREIGN PATENT DOCUMENTS

CN 106446895 A 2/2017
CN 107067396 A 8/2017
(Continued)

OTHER PUBLICATIONS

Christ, Patrick Ferdinand, et al. "Automatic liver and tumor segmentation of CT and MRI volumes using cascaded fully convolutional neural networks." arXiv preprint arXiv:1702.05970 (2017). (Year: 2017).*

(Continued)

*Primary Examiner* — Jonathan S Lee
(74) *Attorney, Agent, or Firm* — Amin, Turocy & Watson, LLP

(57) ABSTRACT

Systems and techniques for facilitating a deep learning architecture for automated image feature extraction are presented. In one example, a system includes a machine learning component. The machine learning component generates learned imaging output regarding imaging data based on a convolutional neural network that receives the imaging data. The machine learning component also performs a plurality of sequential and/or parallel downsampling and upsampling of the imaging data associated with convolutional layers of the convolutional neural network.

20 Claims, 10 Drawing Sheets

(51) Int. Cl.
    *G06N 3/08*           (2006.01)
    *G16H 30/40*         (2018.01)
    *G06N 20/20*         (2019.01)
    *G06K 9/62*           (2006.01)
    *G06T 7/00*           (2017.01)

(52) U.S. Cl.
    CPC ........... *G06N 20/20* (2019.01); *G06T 7/0012* (2013.01); *G16H 30/40* (2018.01); *G06K 2209/05* (2013.01); *G06T 2207/20081* (2013.01); *G06T 2207/20084* (2013.01)

(58) Field of Classification Search
    CPC . G06T 2207/20072; G06T 2207/20081; G06T 2207/20084; G06T 2207/30016; G06T 2210/41; G06T 2210/52; G16H 30/40; G06K 9/46; G06K 9/6202; G06K 9/6212; G06K 9/6215; G06K 9/6256; G06K 9/6267; G06K 9/628; G06N 3/04; G06N 3/0454; G06N 3/08
    USPC .......................................................... 382/158
    See application file for complete search history.

(56) References Cited

U.S. PATENT DOCUMENTS

| | | | |
|---|---|---|---|
| 9,607,373 | B2 | 3/2017 | Buisseret et al. |
| 10,140,544 | B1 | 11/2018 | Zhao et al. |
| 10,192,640 | B2 | 1/2019 | Itu et al. |
| 10,460,447 | B2* | 10/2019 | Song ................. G06T 7/174 |
| 2003/0194124 | A1 | 10/2003 | Suzuki et al. |
| 2009/0082637 | A1 | 3/2009 | Galperin |
| 2012/0051608 | A1 | 3/2012 | Avinash et al. |
| 2012/0070044 | A1 | 3/2012 | Avinash et al. |
| 2016/0300120 | A1 | 10/2016 | Haas et al. |
| 2017/0024641 | A1 | 1/2017 | Wierzynski |
| 2017/0039708 | A1 | 2/2017 | Henry et al. |
| 2017/0185871 | A1 | 6/2017 | Zhang et al. |
| 2017/0200260 | A1 | 7/2017 | Bhaskar et al. |
| 2017/0213339 | A1 | 7/2017 | Hibbard et al. |
| 2017/0270653 | A1 | 9/2017 | Garnavi et al. |
| 2017/0287134 | A1 | 10/2017 | Abedini et al. |
| 2018/0084988 | A1 | 3/2018 | Chakravorty et al. |
| 2018/0247195 | A1 | 8/2018 | Kumar et al. |
| 2018/0253531 | A1 | 9/2018 | Sharma et al. |
| 2018/0263565 | A1 | 9/2018 | Weiss et al. |
| 2018/0315193 | A1 | 11/2018 | Paschalakis et al. |
| 2018/0350066 | A1 | 12/2018 | Zuyev et al. |
| 2018/0360313 | A1 | 12/2018 | Zhang |
| 2019/0005684 | A1 | 1/2019 | De Fauw et al. |
| 2019/0080456 | A1* | 3/2019 | Song ................. G06T 7/12 |
| 2019/0122075 | A1* | 4/2019 | Zhang ................. G06T 7/0016 |
| 2019/0122360 | A1* | 4/2019 | Zhang ................. G06N 3/0454 |
| 2019/0122364 | A1* | 4/2019 | Zhang ................. G06T 7/0016 |

FOREIGN PATENT DOCUMENTS

| | | |
|---|---|---|
| CN | 107256396 A | 10/2017 |
| CN | 107846012 A | 3/2018 |
| WO | 2010/005969 A2 | 1/2010 |
| WO | 106952338 A | 7/2017 |

OTHER PUBLICATIONS

Ravishankar, Hariharan, et al. "Joint deep learning of foreground, background and shape for robust contextual segmentation." International Conference on Information Processing in Medical Imaging. Springer, Cham, 2017. (Year: 2017).*

Abd-Ellah, Mahmoud Khaled, et al. "TPUAR-Net: Two Parallel U-Net with Asymmetric Residual-Based Deep Convolutional Neural Network for Brain Tumor Segmentation." International Conference on Image Analysis and Recognition. Springer, Cham, 2019. (Year: 2019).*

Chen, Shuqing, et al. "Towards automatic abdominal multi-organ segmentation in dual energy CT using cascaded 3D fully convolutional network." arXiv preprint arXiv:1710.05379 (2017). (Year: 2017).*

Wang, Guotai, et al. "Automatic brain tumor segmentation using cascaded anisotropic convolutional neural networks." International MICCAI brainlesion workshop. Springer, Cham, 2017. (Year: 2017).*

Jégou, Simon, et al. "The one hundred layers tiramisu: Fully convolutional densenets for semantic segmentation." Proceedings of the IEEE conference on computer vision and pattern recognition workshops. 2017. (Year: 2017).*

Hwang et al., "Self-Transfer Learning for Fully Weakly Supervised Object Localization," arXiv:1602.01625v1 [cs.CV], Feb. 4, 2016, 9 pages.

Dubost et al., "GP-Unet: Lesion Detection from Weak Labels with a 3D Regression Network", International Conference on Medical Image Computing and Computer-Assisted Intervention, MICCAI, Sep. 4, 2017, pp. 214-221.

Oktay et al., "Anatomically Constrained Neural Networks (ACNN): Application to Cardiac Image Enhancement and Segmentation", IEEE Transactions on Medical Imaging, vol. 37, No. 2, Aug. 29, 2017, pp. 1-13.

Payer et al., "Multi-Label Whole Heart Segmentation Using CNNs and Anatomical Label Configurations", Institute for Computer Graphics and Vision, vol. 10663, 2017, pp. 1-8.

Rohe et al., "Automatic Multi-Atlas Segmentation of Myocardium with SVF-Net", Statistical Atlases and Computational Models of the Heart (STACOM), Aug. 18, 2017, 9 pages.

Wang et al., "ChestX-ray8: Hospital-scale Chest X-ray Database and Benchmarks on Weakly-Supervised Classification and Localization of Common Thorax Diseases", IEEE Conference on Computer Vision and Pattern Recognition (CVPR), Jul. 21, 2017, pp. 3462-3471.

International Search Report and Written Opinion received for PCT Application Serial No. PCT/US2018/018902 dated Jul. 2, 2018, 10 pages.

Non-Final Office Action received for U.S. Appl. No. 15/792,698 dated Mar. 11, 2019, 44 pages.

International Search Report and Written Opinion received for PCT Application Serial No. PCT/US2018/031779 dated Jul. 16, 2018, 9 pages.

Shin et al., "Deep Convolutional Neural Networks for Computer-Aided Detection: CNN Architectures, Dataset Characteristics and Transfer Learning", IEEE Transactions on Medical Imaging, vol. 35, No. 5, 2016, pp. 1-14.

Zhang et al., "Deep Learning Architecture for Automated Image Feature Extraction", U.S. Appl. No. 62/574,333 dated Oct. 19, 2017, 50 pages.

Zhang et al., "Image Analysis Using Deviation From Normal Data", U.S. Appl. No. 15/855,033 dated Dec. 27, 2017, 71 pages.

Zhang et al., "Training an Auto-Encoder on a Single Class", U.S. Appl. No. 15/854,980 dated Dec. 27, 2017, 69 pages.

Aljabar et al., "Multi-atlas based segmentation of brain images: Atlas selection and its effect on accuracy", NeuroImage, vol. 46, No. 3, Jul. 1, 2009, pp. 726-738.

Curiale et al., "Automatic Myocardial Segmentation by Using a Deep Dearning Network in Cardiac MRI", IEEE XLIII Latin American Computer Conference (CLEI), 2017, 6 pages.

International Search Report and Written Opinion received for PCT Application Serial No. PCT/US2018/017407 dated Jul. 4, 2018, 12 pages.

Zhang et al., "Building a Binary Neural Network Architecture", U.S. Appl. No. 15/855,015 dated Dec. 27, 2017, 76 pages.

International Search Report and Written Opinion received for PCT Application Serial No. PCT/US2018/031754 dated Aug. 16, 2018, 10 pages.

Dimitrievski et al., "High resolution depth reconstruction from monocular images and sparse point clouds using deep convolutional neural network", Proceedings of Spie, vol. 10410, 2017, pp. 1-3.

Hosseini et al., "Derivative Kernels: Numerics and Applications", IEEE Transactions on Image Processing, vol. 26, No. 10, 2017, pp. 1-16.

(56) References Cited

OTHER PUBLICATIONS

Notice of Allowance received for U.S. Appl. No. 15/854,980 dated Nov. 15, 2019, 67 pages.
Non-Final Office Action received for U.S. Appl. No. 15/855,033 dated Aug. 21, 2019, 36 pages.
Final Office Action received for U.S. Appl. No. 15/855,033 dated Jan. 14, 2020, 31 pages.
Non-Final Office Action received for U.S. Appl. No. 15/855,033 dated Jun. 9, 2020, 39 pages.

* cited by examiner

DEEP LEARNING ARCHITECTURE FOR AUTOMATED IMAGE FEATURE EXTRACTION

RELATED APPLICATION

This application claims priority to U.S. Provisional Application No. 62/574,333, filed Oct. 19, 2017, and entitled "DEEP LEARNING ARCHITECTURE FOR AUTOMATED IMAGE FEATURE EXTRACTION", the entirety of which is incorporated herein by reference.

TECHNICAL FIELD

This disclosure relates generally to artificial intelligence.

BACKGROUND

Artificial Intelligence (AI) can be employed for classification and/or analysis of digital images. For instance, AI can be employed for image recognition. In certain technical applications, AI can be employed to enhance imaging analysis. In an example, region-of-interest based deep neural networks can be employed to localize a feature in a digital image. However, accuracy and/or efficiency of a classification and/or an analysis of digital images using conventional artificial techniques is generally difficult to achieve. Furthermore, conventional artificial techniques for classification and/or analysis of digital images generally requires labor-intensive processes such as, for example, pixel annotations, voxel level annotations, etc. As such, conventional artificial techniques for classification and/or analysis of digital images can be improved.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

According to an embodiment, a system includes a machine learning component. The machine learning component generates learned imaging output regarding imaging data based on a convolutional neural network that receives the imaging data. The machine learning component also performs a plurality of sequential and/or parallel downsampling and upsampling of the imaging data associated with convolutional layers of the convolutional neural network.

According to another embodiment, a method is provided. The method provides for receiving, by a system comprising a processor, imaging data. The method also provides for performing, by the system, iterative sequential and/or parallel downsampling and upsampling of the imaging data associated with convolutional layers of a convolutional neural network to generate learned imaging output.

According to yet another embodiment, a method is provided. The method provides for receiving, by a system comprising a processor, imaging data that comprises a set of images. The method also provides for training, by the system, a convolutional neural network by performing iterative sequential and/or parallel downsampling and upsampling of the imaging data associated with convolutional layers of the convolutional neural network.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
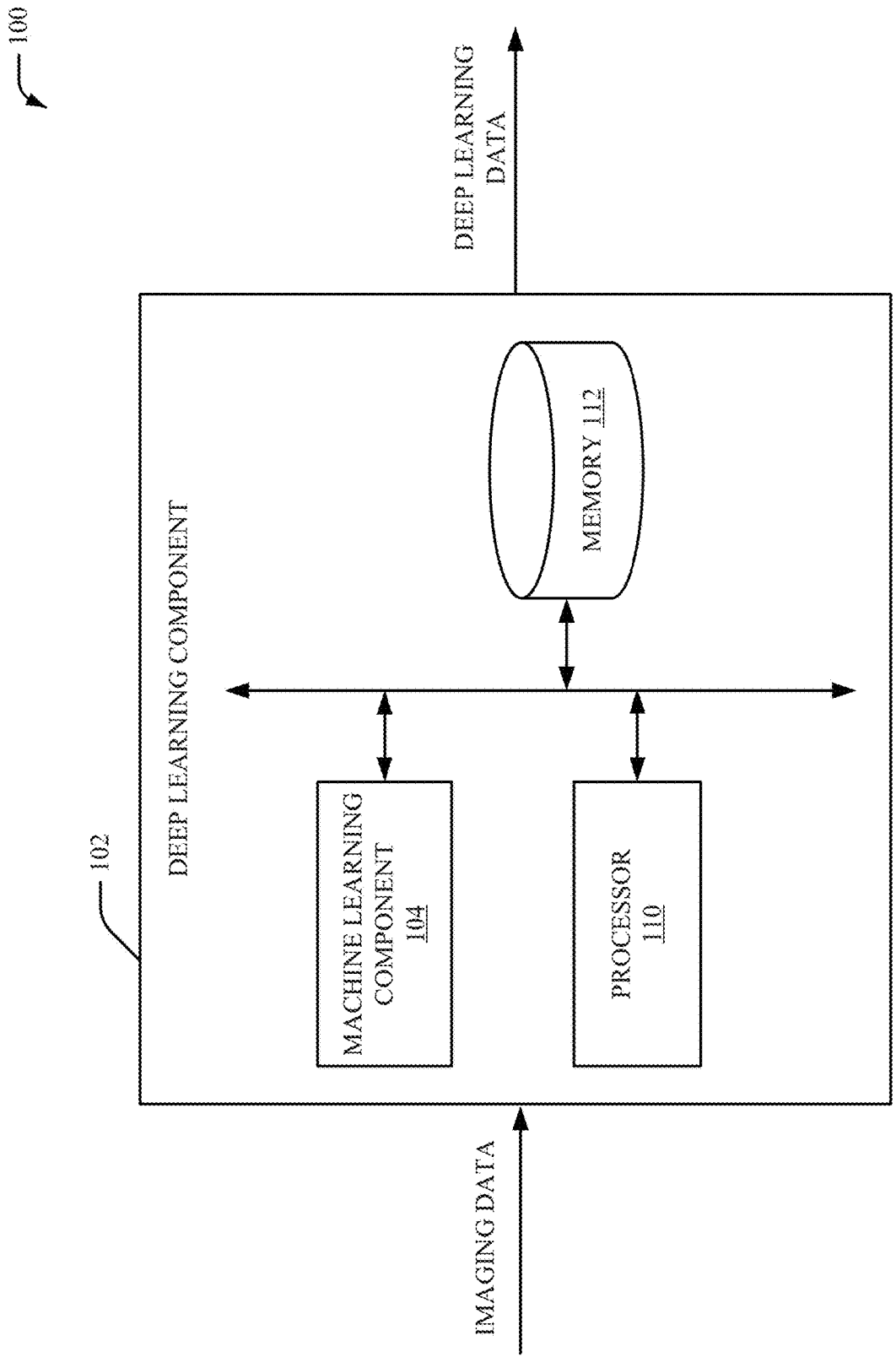
FIG. 1 illustrates a high-level block diagram of an example deep learning component, in accordance with various aspects and implementations described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques that provide a deep learning architecture for automated image feature extraction are presented. For example, as compared to conventional artificial intelligence (AI) techniques, the subject innovations provide for a novel deep learning architecture that provides a versatile and flexible architecture for automated feature extraction for several tasks including, but not limited to, detection, segmentation, and classification. The novel deep learning architecture also provides for automated feature extractors with arbitrary depth and/or width. In an aspect, the deep learning architecture can include a spring network that includes a parallel and/or sequential structure of one or more spring blocks. In an embodiment, the deep learning architecture can include spring blocks arranged in sequential and/or parallel configurations of different (e.g., arbitrary) sizes such that each spring block is configured with a different depth and a different filter size. Therefore, the deep learning architecture can add width to deep learning of the spring network as well as depth to deep learning of the spring network. As such, spring network can capture patterns in data through different ways. Moreover, as compared to conventional deep learning architectures, the novel deep learning architecture disclosed herein can solve feature extraction problems for tasks such as detection, segmentation, and classification. Accordingly, by employing the novel AI framework as described herein, detection and/or localization of one or more features associated with image data (e.g., detection and/or localization of one or more conditions for a patient associated with medical imaging data) can be improved. Furthermore, accuracy and/or efficiency for classification and/or analysis of image data (e.g., medical imaging data) can be improved. Moreover, effectiveness of a machine learning model for classification and/or analysis of image data (e.g., medical imaging data) can be improved, performance of one or more processors that execute a machine learning model for classification and/or analysis of image data (e.g., medical imaging data) can be improved, and/or efficiency of one or more processors that execute a machine learning model for classification and/or analysis of image data (e.g., medical imaging data) can be improved.

Referring to FIG. 1, there is illustrated an example system 100 that provides a deep learning architecture for automated image feature extraction, according to an aspect of the subject disclosure. Repetitive description of like elements employed in other embodiments described herein is omitted for sake of brevity. The system 100 can be employed by various systems, such as, but not limited to medical device systems, medical imaging systems, medical diagnostic systems, medical systems, medical modeling systems, enterprise imaging solution systems, advanced diagnostic tool systems, simulation systems, image management platform systems, care delivery management systems, artificial intelligence systems, machine learning systems, neural network systems, modeling systems, aviation systems, power systems, distributed power systems, energy management systems, thermal management systems, transportation systems, oil and gas systems, mechanical systems, machine systems, device systems, cloud-based systems, heating systems, HVAC systems, medical systems, automobile systems, aircraft systems, water craft systems, water filtration systems, cooling systems, pump systems, engine systems, prognostics systems, machine design systems, and the like. In one example, the system 100 can be associated with a viewer system to facilitate visualization and/or interpretation of imaging data. Moreover, the system 100 and/or the components of the system 100 can be employed to use hardware and/or software to solve problems that are highly technical in nature (e.g., related to processing digital data, related to processing imaging data, related to medical modeling, related to medical imaging, related to artificial intelligence, etc.), that are not abstract and that cannot be performed as a set of mental acts by a human.

The system 100 can include a deep learning component 102 that can include a machine learning component 104. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the deep learning component 102) can include memory 112 for storing computer executable components and instructions. The system 100 (e.g., the deep learning component 102) can further include a processor 110 to facilitate operation of the instructions (e.g., computer executable components and instructions) by the system 100 (e.g., the deep learning component 102).

The deep learning component 102 (e.g., the machine learning component 104) can receive imaging data (e.g., IMAGING DATA shown in FIG. 1). The imaging data can be two-dimensional imaging data and/or three-dimensional imaging data generated by one or more imaging devices. For instance, the imaging data can be imagery captured via a set of sensors (e.g., a set of sensors associated with an imaging device). In certain embodiments, the imaging data can be a series of imagery captured via a set of sensors (e.g., a set of sensors associated with an imaging device) during an interval of time. The imaging data can be received directly from one or more imaging devices. Alternatively, the imaging data can be stored in one or more databases that receives and/or stores the imaging data associated with the one or more imaging devices. In certain embodiments, the image data can be medical imaging data. For example, the image data can be two-dimensional medical imaging data and/or three-dimensional medical imaging data generated by one or more medical imaging devices. In example, the image data can be electromagnetic radiation imagery captured via a set of sensors (e.g., a set of sensors associated with a medical imaging device). In certain embodiments, the image data can be a series of electromagnetic radiation imagery captured via a set of sensors (e.g., a set of sensors associated with a medical imaging device) during an interval of time. In another example, the image data can be positron emission tomography (PET) scan imagery. In yet another example, the image data can be magnetic resonance imaging (MRI) data. The image data can be received directly from one or more medical imaging devices. Alternatively, the image data can be stored in one or more databases that receives and/or stores the medical imaging data associated with the one or more medical imaging devices. A medical imaging device can be, for example, an x-ray device, a computed tomography (CT) device, a PET scanner device, an MRI device, another type of medical imaging device, etc.

The machine learning component 104 can perform a machine learning process (e.g., an artificial intelligence process for machine learning) based on the imaging data. In an aspect, the machine learning component 104 can perform deep learning to facilitate classification and/or localization of one or more features associated with the imaging data. In another aspect, the machine learning component 104 can perform deep learning based on a convolutional neural network that receives the imaging data. In an embodiment, the machine learning component 104 can perform a training phase for the machine learning process. For example, the imaging data can be a set of images stored in a data store.

Furthermore, the machine learning component 104 can perform the training phase for the machine learning process based on the set of images stored in a data store to train a neural network model (e.g., a neural network model for the convolutional neural network). In certain embodiments, the machine learning component 104 can employ a first portion of the imaging data for training associated with the convolutional neural network, a second portion of the imaging data for validation associated with the convolutional neural network, and a third portion of the imaging data for testing associated with the convolutional neural network. Additionally or alternatively, the machine learning component 104 can randomly select a set of images from a training set associated with the imaging data for data augmentation associated with the imaging data. In an aspect, the machine learning component 104 can modify an orientation of the set of images for the data augmentation associated with the imaging data. In one example, the machine learning component 104 can modify the set of images through at least one affine transformation for the data augmentation associated with the imaging data. In another embodiment, the machine learning component 104 can perform an inference phase. Furthermore, the machine learning component 104 can perform the training phase for the machine learning process based on the image. For an inference phase associated with the machine learning component 104, the machine learning component 104 can generate learned imaging output based on the convolutional neural network that receives imaging data.

In an aspect, the machine learning component 104 can employ a spring network of convolutional layers. The machine learning component 104 can employ the spring network of convolutional layers to generate the learned imaging output based on the imaging data. In an aspect, the machine learning component 104 can generate the learned imaging output based on a first convolutional layer process associated with sequential and/or parallel downsampling of the imaging data and a second convolutional layer process associated with sequential and/or parallel upsampling of the imaging data. The spring network of convolutional layers can include the first convolutional layer process associated with the sequential and/or parallel downsampling and the second convolutional layer process associated with sequential and/or parallel upsampling. In one example, the machine learning component 104 can perform a plurality of sequential and/or parallel downsampling and upsampling of the imaging data associated with convolutional layers of the convolutional neural network. The spring network of convolutional layers employed by the machine learning component 104 can alter convolutional layer filters similar to functionality of a spring. For instance, the machine learning component 104 can analyze the imaging data based on a first convolutional layer filter that comprises a first size, a second convolutional layer filter that comprises a second size that is different than the first size, and a third convolutional layer filter that comprises the first size associated with the first convolutional layer filter.

In an embodiment, the machine learning component 104 can generate learned imaging output regarding based on a convolutional neural network that receives the imaging data. The machine learning component 104 can also perform a plurality of sequential and/or parallel downsampling and upsampling of the imaging data associated with convolutional layers of the convolutional neural network. In an aspect, the machine learning component 104 can analyze the imaging data based on a first convolutional layer process that comprises a first depth and a second convolutional layer process that comprises a second depth. In one example, the first convolutional layer process can comprise first filter sizes and the second convolutional layer process can comprise second filter sizes that are different than the first filter sizes. In an embodiment, the machine learning component 104 can perform the first convolutional layer process and the second convolutional layer process sequentially. In another embodiment, the machine learning component 104 can perform the first convolutional layer process and the second convolutional layer process in parallel.

In certain embodiments, the machine learning component 104 can extract information that is indicative of correlations, inferences and/or expressions from the imaging data based on the spring network of convolutional layers. The machine learning component 104 can generate the learned imaging output based on the execution of at least one machine learning model associated with the spring network of convolutional layers. The learned imaging output generated by the machine learning component 104 can include, for example, learning, correlations, inferences and/or expressions associated with the imaging data. In an aspect, the machine learning component 104 can perform learning with respect to the imaging data explicitly or implicitly using the spring network of convolutional layers. The machine learning component 104 can also employ an automatic classification system and/or an automatic classification process to facilitate analysis of the imaging data. For example, the machine learning component 104 can employ a probabilistic and/or statistical-based analysis (e.g., factoring into the analysis utilities and costs) to learn and/or generate inferences with respect to the imaging data. The machine learning component 104 can employ, for example, a support vector machine (SVM) classifier to learn and/or generate inferences for imaging data. Additionally or alternatively, the machine learning component 104 can employ other classification techniques associated with Bayesian networks, decision trees and/or probabilistic classification models. Classifiers employed by the machine learning component 104 can be explicitly trained (e.g., via a generic training data) as well as implicitly trained (e.g., via receiving extrinsic information). For example, with respect to SVM's, SVM's can be configured via a learning or training phase within a classifier constructor and feature selection module. A classifier can be a function that maps an input attribute vector, $x=(x1, x2, x3, x4, xn)$, to a confidence that the input belongs to a class—that is, $f(x)=$confidence(class).

To facilitate localization of one or more features associated with the imaging data, the machine learning component 104 can perform a local pooling process for an activation map associated with a convolutional layer of the convolutional neural network prior to performing a global pooling process associated with the convolutional neural network. Additionally or alternatively, the machine learning component 104 can generate the learned imaging output based on a class activation mapping process that applies a set of weights to a set of heat maps associated with the imaging data. Additionally or alternatively, the machine learning component 104 can process the imaging data based on one or more regularization techniques to classify one or more portions of the imaging data. In an aspect, the machine learning component 104 can also merge a set of classifier layers associated with the convolutional neural network and a set of activation maps associated with the convolutional neural network to generate the learned imaging output.

In an embodiment, the deep learning component 102 (e.g., the machine learning component 104) can generate deep learning data (e.g., DEEP LEARNING DATA shown in FIG.

1). In an embodiment, the deep learning data can include a classification and/or a location for one or more features located in the imaging data. In certain embodiments, the deep learning data can include probability data indicative of a probability for one or more features being located in the imaging data. The probability data can be, for example, a probability array of data values for one or more features being located in the imaging data. In certain embodiments, the deep learning component 102 (e.g., the machine learning component 104) can perform deep learning to facilitate classification and/or localization of one or more conditions associated with the imaging data. A condition classified and/or localized by the deep learning component 102 (e.g., the machine learning component 104) can include, for example, a lung disease, a heart disease, a tissue disease, a bone disease, a tumor, a cancer, tuberculosis, cardiomegaly, hypoinflation of a lung, opacity of a lung, hyperdistension, a spine degenerative disease, calcinosis, or another type of condition associated with an anatomical region of a patient body. In an aspect, the deep learning component 102 (e.g., the machine learning component 104) can determine a prediction for a condition associated with the imaging data. For example, the deep learning component 102 (e.g., the machine learning component 104) can determine a probability score for a condition associated with the imaging data (e.g., a first percentage value representing likelihood of a negative prognosis for the condition and a second value representing a likelihood of a positive prognosis for the condition).

It is to be appreciated that technical features of the deep learning component 102 are highly technical in nature and not abstract ideas. Processing threads of the deep learning component 102 that process and/or analyze the imaging data, determine deep learning data, etc. cannot be performed by a human (e.g., are greater than the capability of a single human mind). For example, the amount of the imaging data processed, the speed of processing of the imaging data and/or the data types of the imaging data processed by the deep learning component 102 over a certain period of time can be respectively greater, faster and different than the amount, speed and data type that can be processed by a single human mind over the same period of time. Furthermore, the imaging data processed by the deep learning component 102 can be one or more images generated by sensors of an imaging device. Moreover, the deep learning component 102 can be fully operational towards performing one or more other functions (e.g., fully powered on, fully executed, etc.) while also processing the imaging data.

Figure 2:
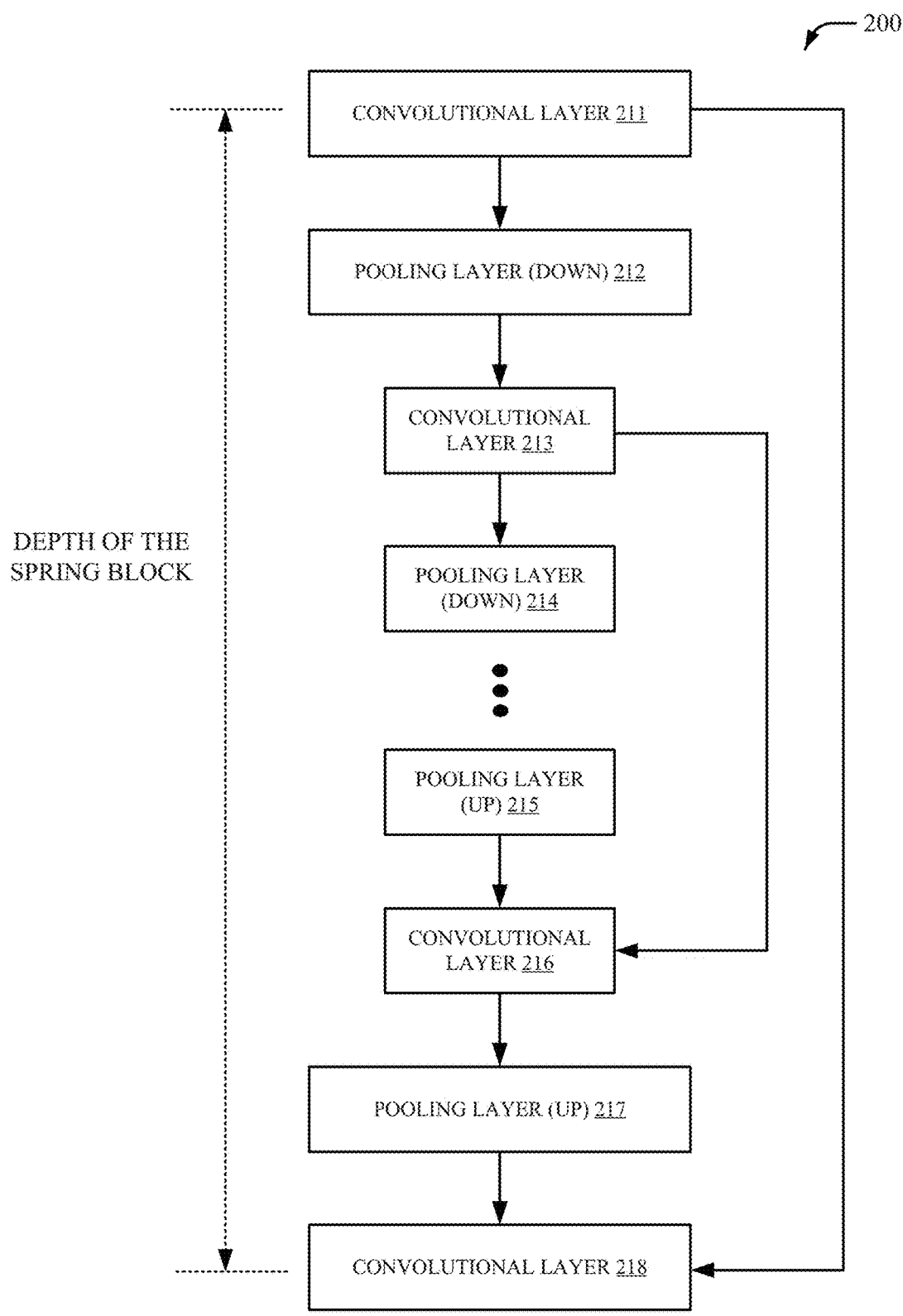
FIG. 2 illustrates a high-level block diagram of an example spring block, in accordance with various aspects and implementations described herein.

Referring now to FIG. 2, there is illustrated a non-limiting implementation of a system 200 in accordance with various aspects and implementations of this disclosure. The system 200 can illustrate an example spring block for a deep learning architecture. For example, the system 200 can illustrate an example spring block associated with a convolutional neural network. As disclosed herein, a "spring block" can be a convolutional layer process associated with a convolutional neural network. Furthermore, it is to be appreciated that "spring block" and "convolutional layer process" are referred to interchangeably herein. In an embodiment, the system 200 can be employed by the machine learning component 104. The spring block associated with the system 200 can be associated with sequential upsampling and downsampling for a spring deep learning network. In an aspect, the spring block associated with the system 200 can consist of connected pair down sampling/up sampling layers and convolutional layers. The spring block associated with the system 200 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.).

In an embodiment, the system 200 can include a convolutional layer 211. The convolutional layer 211 can be a first convolutional layer of a convolutional neural network that processes imaging data. Furthermore, the convolutional layer 211 can be associated with a first filter size. The convolutional layer 211 can be followed by a pooling layer (down) 212. The pooling layer (down) 212 can be associated with downsampling. For instance, the pooling layer (down) 212 can reduce dimensionality of data generated by the convolutional layer 211. In one example, the pooling layer (down) 212 can reduce dimensionality of a feature map for imaging data processed by the convolutional layer 211. The pooling layer (down) 212 can be followed by a convolutional layer 213. The convolutional layer 213 can be a second convolutional layer of the convolutional neural network that processes the imaging data. Furthermore, the convolutional layer 213 can be associated with a second filter size that is different than the first filter size associated with the convolutional layer 211. For example, the second filter size associated with the convolutional layer 213 can be smaller than the first filter size associated with the convolutional layer 211. The convolutional layer 213 can be followed by a pooling layer (down) 214. The pooling layer (down) 214 can be associated with downsampling. For instance, the pooling layer (down) 214 can reduce dimensionality of data generated by the convolutional layer 213. In one example, the pooling layer (down) 214 can reduce dimensionality of a feature map for imaging data processed by the convolutional layer 213. The pooling layer (down) 214 can be followed by a convolutional layer (not shown), which, in turn, can be followed by a pooling layer (up) 215. However, in certain embodiments, the pooling layer (down) 214 can be followed by one or more other convolutional layers and/or one or more other pooling layers (down) prior to the pooling layer (up) 215 to further process imaging data with different filter sizes and/or further reduction to dimensionality of data. The pooling layer (up) 215 can be associated with upsampling. For instance, the pooling layer (up) 215 can increase dimensionality of data generated by one or more convolutional layers. In one example, the pooling layer (up) 215 can increase dimensionality of a feature map for imaging data processed by one or more convolutional layers. The pooling layer (up) 215 can be followed by a convolutional layer 216. The convolutional layer 216 can be, for example, a third convolutional layer of the convolutional neural network that processes the imaging data. Furthermore, the convolutional layer 216 can be associated with the second filter size associated with the convolutional layer 213.

The convolutional layer 216 can be followed by a pooling layer (up) 217. The pooling layer (up) 217 can be associated with upsampling. For instance, the pooling layer (up) 217 can increase dimensionality of data generated by the convolutional layer 216. In one example, the pooling layer (up) 217 can increase dimensionality of a feature map for imaging data processed by the convolutional layer 216. The pooling layer (up) 217 can be followed by a convolutional layer 218. The convolutional layer 218 can be, for example, a fourth convolutional layer of the convolutional neural network that processes the imaging data. Furthermore, the convolutional layer 218 can be associated with the first filter size associated with the convolutional layer 216. As such, the spring block associated with the system 200 can behave similar to functionality of a spring where a filter size for one or more convolutional layers are repeated while processing imaging data via a convolutional neural network.

Figure 3:
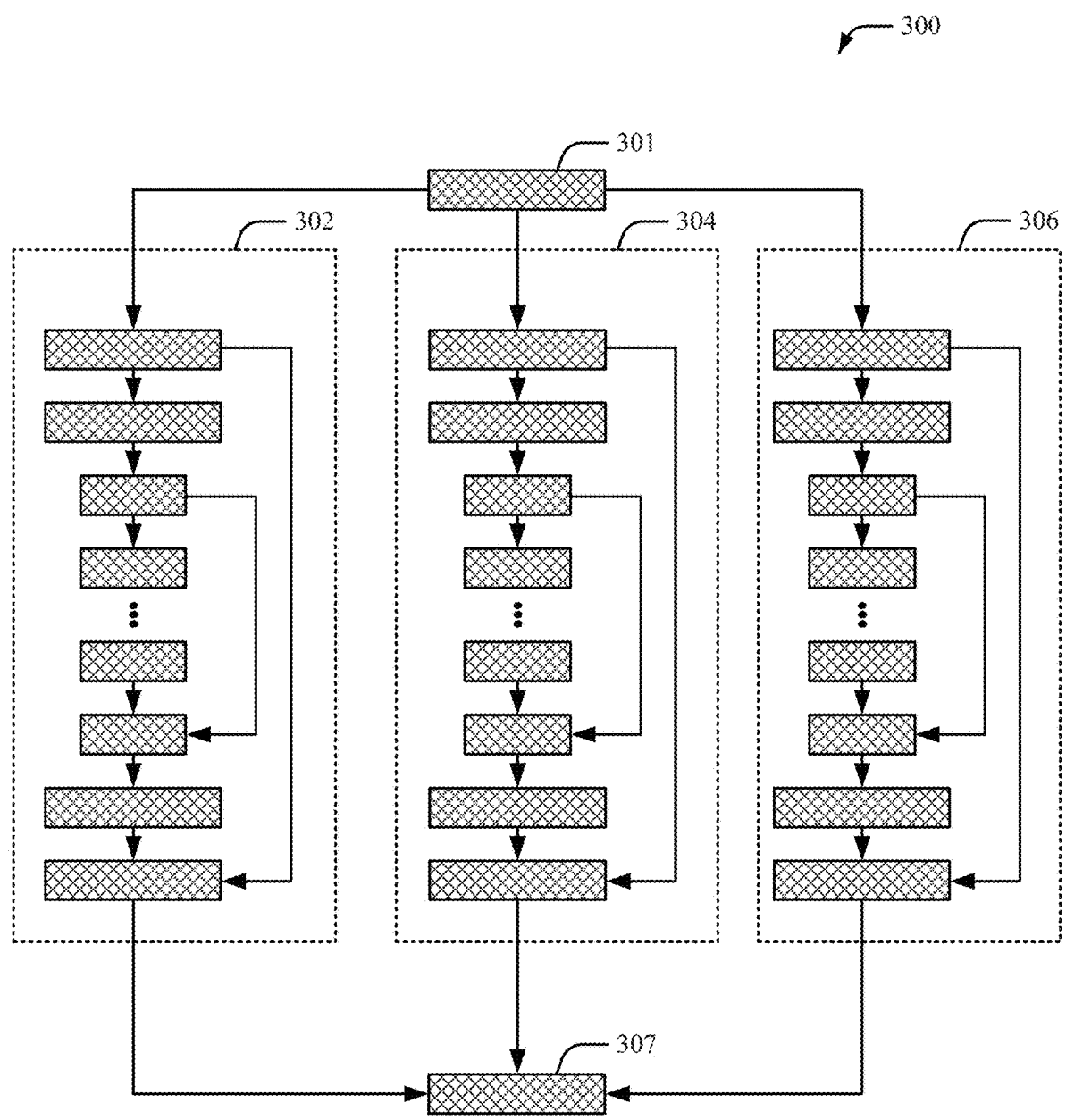
FIG. 3 illustrates a high-level block diagram of an example parallel structure of spring blocks, in accordance with various aspects and implementations described herein.

Referring now to FIG. 3, there is illustrated a non-limiting implementation of a system 300 in accordance with various aspects and implementations of this disclosure. Repetitive description of like elements employed in other embodiments described herein is omitted for sake of brevity. In an embodiment, the system 300 can be employed by the machine learning component 104. The system 300 can be a deep learning network (e.g., a convolutional neural network) that includes a parallel structure of spring blocks. For example, the system 300 can be a parallel network made up of spring blocks. It is to be appreciated that the system 300 can be constructed in various parallel spring block arrangements. In an embodiment, the system 300 can include a first convolutional layer process 302 that comprises a first depth, a second convolutional layer process 304 that comprises a second depth, and a third convolutional layer process 306 that comprises a third depth. The first convolutional layer process 302, the second convolutional layer process 304, and the third convolutional layer process 306 can be performed in parallel. For example, the first convolutional layer process 302 can be performed in parallel to the second convolutional layer process 304 and the third convolutional layer process 306. Furthermore, the second convolutional layer process 304 can be performed in parallel to the first convolutional layer process 302 and the third convolutional layer process 306. Moreover, the third convolutional layer process 306 can be performed in parallel to the first convolutional layer process 302 and the second convolutional layer process 304.

In an aspect, the first convolutional layer process 302 can be associated with sequential upsampling and downsampling. For example, the first convolutional layer process 302 can consist of connected pair down sampling/up sampling layers and convolutional layers. The first convolutional layer process 302 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.). Additionally, the second convolutional layer process 304 can be associated with sequential upsampling and downsampling. For example, the second convolutional layer process 304 can consist of connected pair down sampling/up sampling layers and convolutional layers. The second convolutional layer process 304 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.). Moreover, the third convolutional layer process 306 can be associated with sequential upsampling and downsampling. For example, the third convolutional layer process 306 can consist of connected pair down sampling/up sampling layers and convolutional layers. The third convolutional layer process 306 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.).

In certain embodiments, the first convolutional layer process 302, the second convolutional layer process 304, and the third convolutional layer process 306 can include different filter sizes. For example, the first depth associated with the first convolutional layer process 302 can be different than the second depth associated with the second convolutional layer process 304 and/or the third depth associated with the third convolutional layer process 306. In another example, the second depth associated with the second convolutional layer process 304 can be different than the first depth associated with the first convolutional layer process 302 and/or the third depth associated with the third convolutional layer process 306. In yet another example, the third depth associated with the third convolutional layer process 306 can be different than the first depth associated with the first convolutional layer process 302 and/or the second depth associated with the second convolutional layer process 304. In certain embodiments, a concatenation step 301 can be performed prior to the first convolutional layer process 302, the second convolutional layer process 304, and/or the third convolutional layer process 306. Additionally or alternatively, in certain embodiments, a concatenation step 307 can be performed prior to the first convolutional layer process 302, the second convolutional layer process 304, and/or the third convolutional layer process 306.

Figure 4:
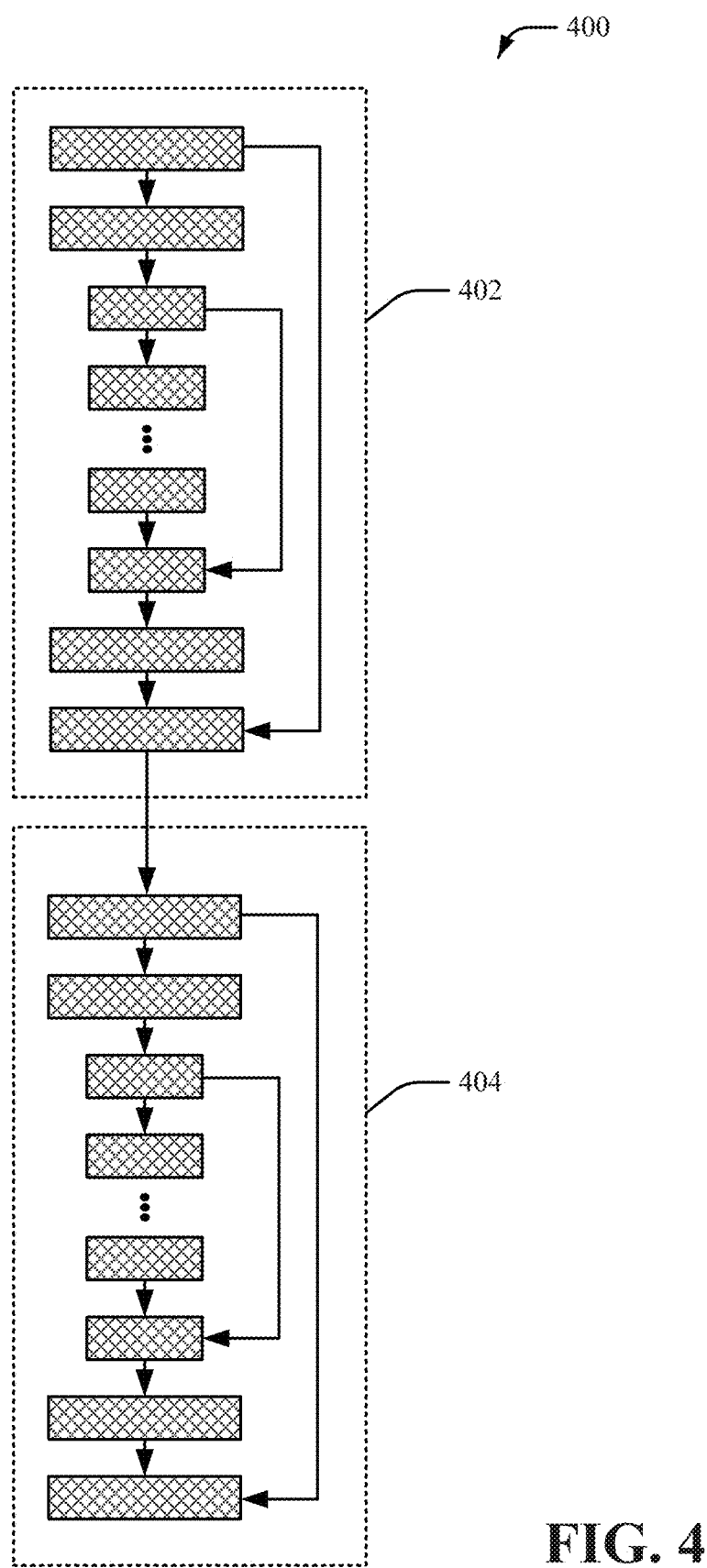
FIG. 4 illustrates a high-level block diagram of an example sequential structure of spring blocks, in accordance with various aspects and implementations described herein.

Referring now to FIG. 4, there is illustrated a non-limiting implementation of a system 400 in accordance with various aspects and implementations of this disclosure. Repetitive description of like elements employed in other embodiments described herein is omitted for sake of brevity. In an embodiment, the system 400 can be employed by the machine learning component 104. The system 400 can be a deep learning network (e.g., a convolutional neural network) that includes a sequential structure of spring blocks. For example, the system 400 can be a sequential network made up of spring blocks. It is to be appreciated that the system 400 can be constructed in various sequential spring block arrangements. In an embodiment, the system 400 can include a first convolutional layer process 402 that comprises a first depth and a second convolutional layer process 404 that comprises a second depth. The first convolutional layer process 402 and the second convolutional layer process 404 can be performed in parallel. Furthermore, in certain embodiments, the first convolutional layer process 402 and the second convolutional layer process 404 can include different filter sizes. For example, the first depth associated with the first convolutional layer process 402 can be different than the second depth associated with the second convolutional layer process 404.

In an embodiment, the first convolutional layer process 402 can be associated with sequential upsampling and downsampling. For example, the first convolutional layer process 402 can consist of connected pair down sampling/up sampling layers and convolutional layers. The first convolutional layer process 402 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.). Additionally, the second convolutional layer process 404 can be associated with sequential upsampling and downsampling. For example, the second convolutional layer process 404 can consist of connected pair down sampling/up sampling layers and convolutional layers. The second convolutional layer process 404 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.). In certain embodiments, a convolutional layer of the second convolutional layer process 404 can be coupled to a convolutional layer of the first convolutional layer process 402.

Figure 5:
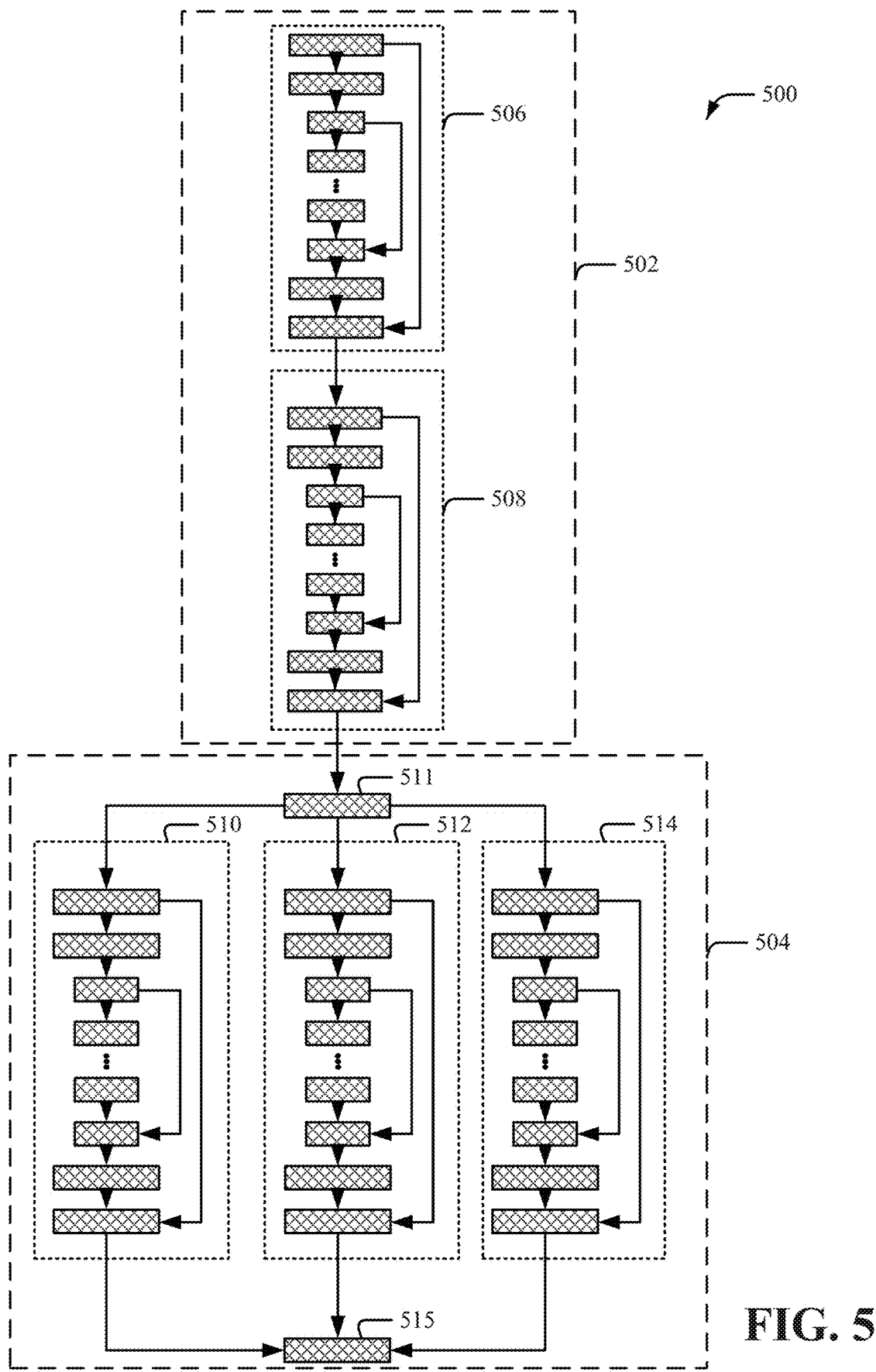
FIG. 5 illustrates a high-level block diagram of an example spring network for a deep learning architecture, in accordance with various aspects and implementations described herein.

Referring now to FIG. 5, there is illustrated a non-limiting implementation of a system 500 in accordance with various aspects and implementations of this disclosure. Repetitive description of like elements employed in other embodiments described herein is omitted for sake of brevity. In an embodiment, the system 500 can be employed by the machine learning component 104. The system 500 can be a deep learning network (e.g., a convolutional neural network) that includes a parallel and sequential structure of spring blocks. For example, the system 500 can be a parallel and sequential network made up of spring blocks. It is to be appreciated that the system 500 can be constructed in various parallel and sequential spring block arrangements. In an embodiment, the system 500 can be, for example, a springNetXT network. In an aspect, the system 500 can be a spring network that includes a parallel and sequential structure of one or more spring blocks. Therefore, the system 500 can add width to deep learning of as well as depth to deep learning. Furthermore, the system 500 can capture patterns in data (e.g., imaging data) through different ways.

In an embodiment, the system 500 can include a sequential structure 502 of spring blocks and a parallel structure 504 of spring blocks. The sequential structure 502 of spring blocks can be coupled to the parallel structure 504 of spring blocks. For example, the parallel structure 504 of spring blocks can be performed after processing of the sequential structure 502 of spring blocks. In an implementation, the sequential structure 502 of spring blocks can include a first convolutional layer process 506 that comprises a first depth and a second convolutional layer process 508 that comprises a second depth. The first convolutional layer process 506 and the second convolutional layer process 508 can be performed in parallel. Furthermore, in certain embodiments, the first convolutional layer process 506 and the second convolutional layer process 508 can include different filter sizes. For example, the first depth associated with the first convolutional layer process 506 can be different than the second depth associated with the second convolutional layer process 508. In an embodiment, the first convolutional layer process 506 can be associated with sequential upsampling and downsampling. For example, the first convolutional layer process 506 can consist of connected pair down sampling/up sampling layers and convolutional layers. The first convolutional layer process 506 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.). Additionally, the second convolutional layer process 508 can be associated with sequential upsampling and downsampling. For example, the second convolutional layer process 508 can consist of connected pair down sampling/up sampling layers and convolutional layers. The second convolutional layer process 508 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.). In certain embodiments, a convolutional layer of the second convolutional layer process 508 can be coupled to a convolutional layer of the first convolutional layer process 506.

Additionally, the parallel structure 504 of spring blocks can include a first convolutional layer process 510 that comprises a first depth, a second convolutional layer process 512 that comprises a second depth, and a third convolutional layer process 514 that comprises a third depth. The first convolutional layer process 510, the second convolutional layer process 512, and the third convolutional layer process 514 can be performed in parallel. For example, the first convolutional layer process 510 can be performed in parallel to the second convolutional layer process 512 and the third convolutional layer process 514. Furthermore, the second convolutional layer process 512 can be performed in parallel to the first convolutional layer process 510 and the third convolutional layer process 514. Moreover, the third convolutional layer process 514 can be performed in parallel to the first convolutional layer process 510 and the second convolutional layer process 512.

In an aspect, the first convolutional layer process 510 can be associated with sequential upsampling and downsampling. For example, the first convolutional layer process 510 can consist of connected pair down sampling/up sampling layers and convolutional layers. The first convolutional layer process 510 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.). Additionally, the second convolutional layer process 512 can be associated with sequential upsampling and downsampling. For example, the second convolutional layer process 512 can consist of connected pair down sampling/up sampling layers and convolutional layers. The second convolutional layer process 512 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.). Moreover, the third convolutional layer process 514 can be associated with sequential upsampling and downsampling. For example, the third convolutional layer process 514 can consist of connected pair down sampling/up sampling layers and convolutional layers. The third convolutional layer process 514 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.).

In certain embodiments, the first convolutional layer process 510, the second convolutional layer process 512, and the third convolutional layer process 514 can include different filter sizes. For example, the first depth associated with the first convolutional layer process 510 can be different than the second depth associated with the second convolutional layer process 512 and/or the third depth associated with the third convolutional layer process 514. In another example, the second depth associated with the second convolutional layer process 512 can be different than the first depth associated with the first convolutional layer process 510 and/or the third depth associated with the third convolutional layer process 514. In yet another example, the third depth associated with the third convolutional layer process 514 can be different than the first depth associated with the first convolutional layer process 510 and/or the second depth associated with the second convolutional layer process 512. In certain embodiments, a concatenation step 511 can be performed prior to the first convolutional layer process 510, the second convolutional layer process 512, and/or the third convolutional layer process 514. Additionally or alternatively, in certain embodiments, a concatenation step 515 can be performed prior to the first convolutional layer process 510, the second convolutional layer process 512, and/or the third convolutional layer process 514.

It is to be appreciated that a deep learning network with parallel and/or sequential spring block arrangements as disclosed herein is very flexible. Furthermore, a deep learning network with parallel and/or sequential spring block arrangements as disclosed herein can include parameters such as, for example, a number of parallel spring blocks. Additionally or alternatively, a deep learning network with parallel and/or sequential spring block arrangements as disclosed herein can include parameters such as, for example, for each parallel spring block, a depth (e.g., a number of pooling layers and a number of convolutional layers) and convolutional filter sizes. Additionally or alternatively, a deep learning network with parallel and/or sequential spring block arrangements as disclosed herein can include parameters such as, for example, a number of sequential spring blocks. Additionally or alternatively, a deep learning network with parallel and/or sequential spring block arrangements as disclosed herein can include parameters such as, for example, within sequential spring blocks, a depth and convolutional filter sizes.

Figure 6:
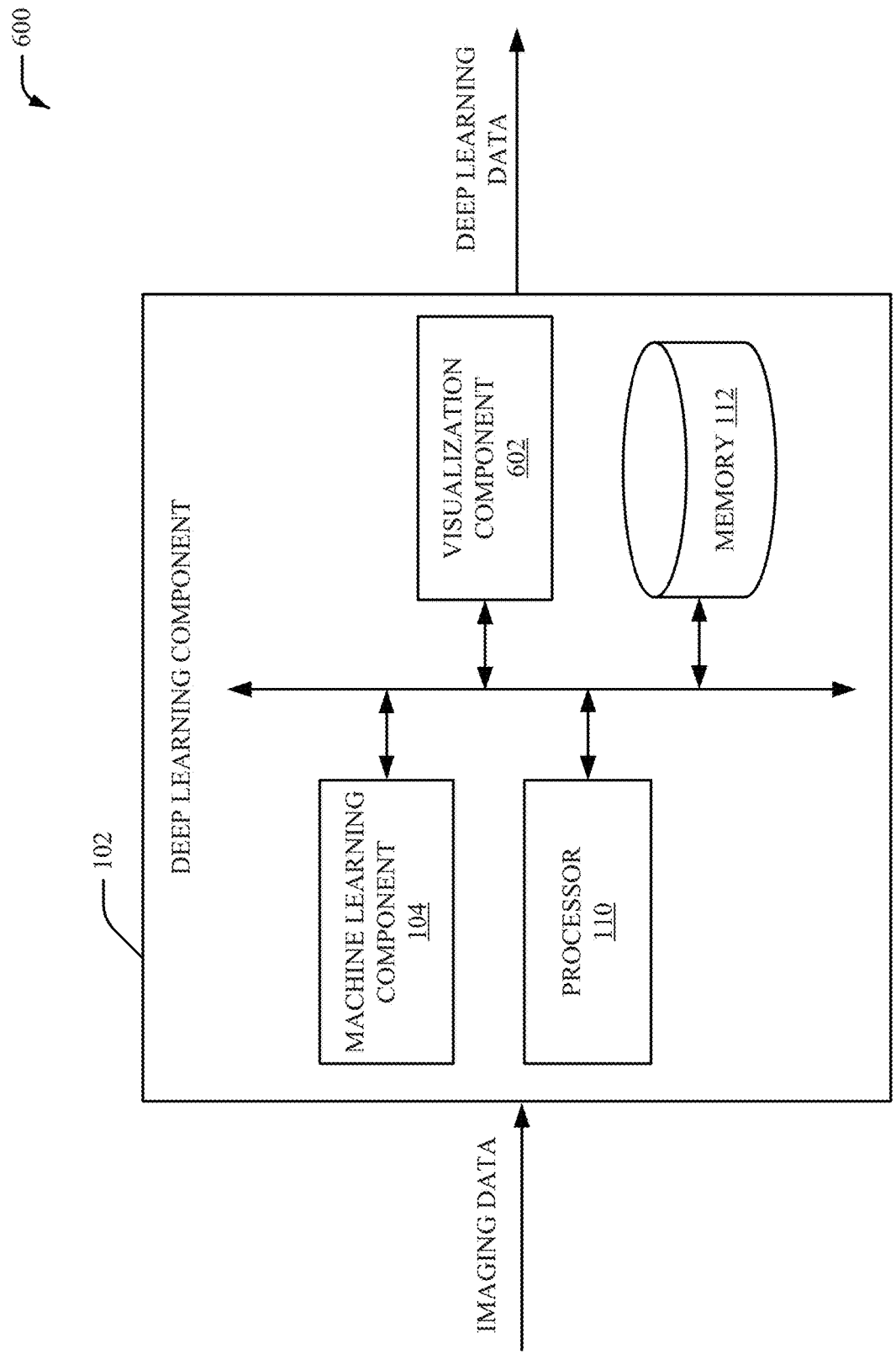
FIG. 6 illustrates a high-level block diagram of another example deep learning component, in accordance with various aspects and implementations described herein.

Referring now to FIG. 6, there is illustrated a non-limiting implementation of a system 600 in accordance with various aspects and implementations of this disclosure. Repetitive description of like elements employed in other embodiments described herein is omitted for sake of brevity.

The system 600 includes the deep learning component 102. The deep learning component 102 can include the machine learning component 104, the processor 110, the memory 112 and/or a visualization component 602. The visualization component 602 can generate a human-interpretable visualization of the deep learning data. In an embodiment, the visualization component 602 can generate a multi-dimensional visualization associated with a classification and/or a location for one or more features located in the imaging data. In certain embodiments, the visualization component 602 can generate a multi-dimensional visualization associated with a classification and/or a location for a portion of an anatomical region associated with the imaging data. For example, the visualization component 602 can generate a multi-dimensional visualization associated with a classification and/or a location for one or more conditions located in the imaging data.

The multi-dimensional visualization can be a graphical representation of a classification and/or a location for one or more features located in the imaging data. The visualization component 602 can also generate a display of the multi-dimensional visualization of a classification and/or a location for one or more features located in the imaging data. In certain embodiments, the multi-dimensional visualization can be a graphical representation of the imaging data that shows a classification and/or a location of one or more conditions with respect to a patient body. In an aspect, the visualization component 602 can render a 2D visualization of a classification and/or a location for one or more features on a user interface associated with a display of a user device such as, but not limited to, a computing device, a computer, a desktop computer, a laptop computer, a monitor device, a smart device, a smart phone, a mobile device, a handheld device, a tablet, a portable computing device or another type of user device associated with a display.

In one example, the visualization component 602 can render a 2D visualization of a portion of an anatomical region on a user interface associated with a display of a user device such as, but not limited to, a computing device, a computer, a desktop computer, a laptop computer, a monitor device, a smart device, a smart phone, a mobile device, a handheld device, a tablet, a portable computing device or another type of user device associated with a display. In another aspect, the multi-dimensional visualization can include the deep learning data. In yet another aspect, the deep learning data can also be rendered on the 3D model as one or more dynamic visual elements. The visualization component 602 can, in an embodiment, alter visual characteristics (e.g., color, size, hues, shading, etc.) of at least a portion of the deep learning data associated with the multi-dimensional visualization based on a classification and/or a location for one or more features located in the imaging data. For example, a classification and/or a location for one or more features located in the imaging data can be presented as different visual characteristics (e.g., colors, sizes, hues or shades, etc.), based on a result of deep learning by the deep learning component 102. In another aspect, the visualization component 602 can allow a user to zoom into or out with respect to the deep learning data associated with the multi-dimensional visualization. For example, the visualization component 602 can allow a user to zoom into or out with respect to a classification and/or a location for one or more features located in the imaging data. In one example, the visualization component 602 can allow a user to zoom into or out with respect to a classification and/or a location of one or more conditions identified in the anatomical region of the patient body. As such, a user can view, analyze and/or interact with the deep learning data associated with the multi-dimensional visualization.

Figure 7:
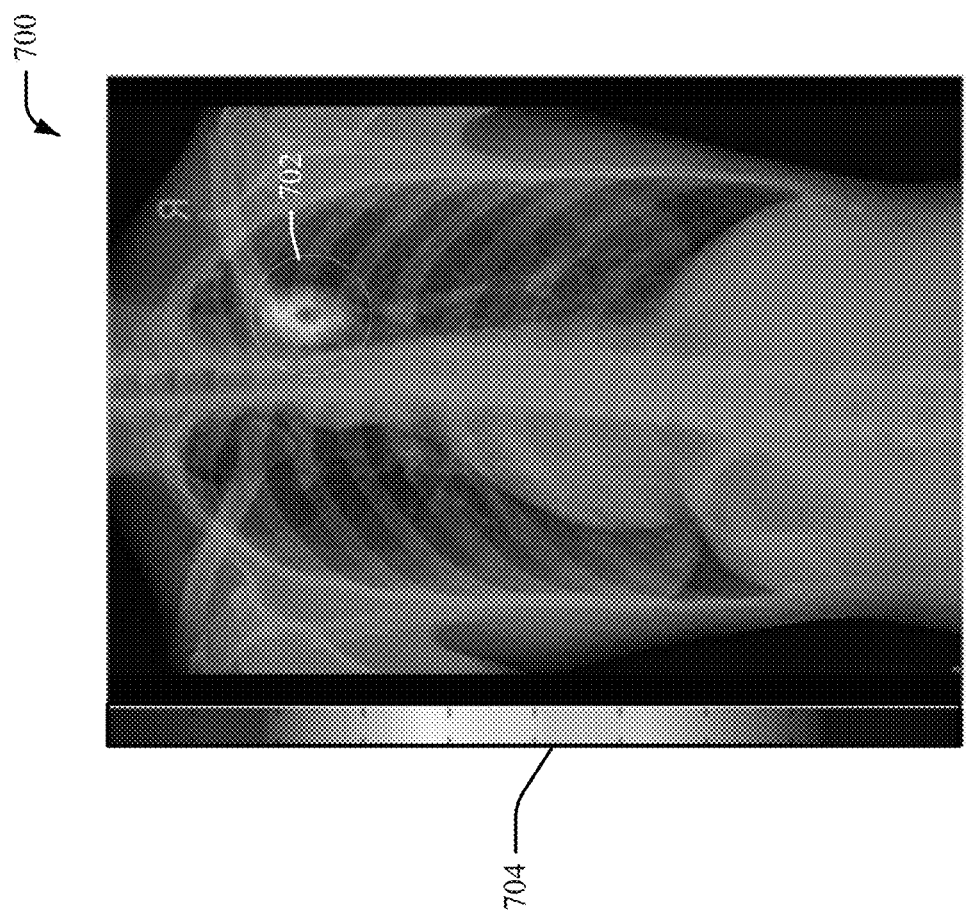
FIG. 7 illustrates an example multi-dimensional visualization, in accordance with various aspects and implementations described herein.

FIG. 7 illustrates an example multi-dimensional visualization 700, in accordance with various aspects and implementations described herein. In the embodiment shown in FIG. 7, the multi-dimensional visualization 700 can, for example, display a medical imaging diagnosis for a patient. For example, the multi-dimensional visualization 700 can display one or more classifications and/or one or more localizations for one or more conditions identified in imaging data (e.g., medical imaging data). However, it is to be appreciated that the multi-dimensional visualization 700 can be associated with another type of classification and/or location for one or more features located in imaging data. In an aspect, the multi-dimensional visualization 700 can include localization data 702 for a medical imaging diagnosis. The localization data 702 can be a predicted location for a condition associated with imaging data processed by the deep learning component 102 (e.g., the machine learning component 104). Visual characteristics (e.g., a color, a size, hues, shading, etc.) of the localization data 702 can be dynamic based on information provided by the deep learning component 102 (e.g., the machine learning component 104). For instance, a first portion of the localization data 702 can comprise a first visual characteristic, a second portion of the localization data 702 can comprise a second visual characteristic, a third portion of the localization data 702 can comprise a third visual characteristic, etc. In an embodiment, a display environment associated with the multi-dimensional visualization 700 can include a heat bar 704. The heat bar 704 can include a set of colors that correspond to different values for the localization data 702. For example, a first color (e.g., a color red) in the heat bar 704 can correspond to a first value for the localization data 702, a second color (e.g., a color green) in the heat bar 704 can correspond to a second value for the localization data 702, a third color (e.g., a color blue) in the heat bar 704 can correspond to a third value for the localization data 702, etc.

Figure 8:
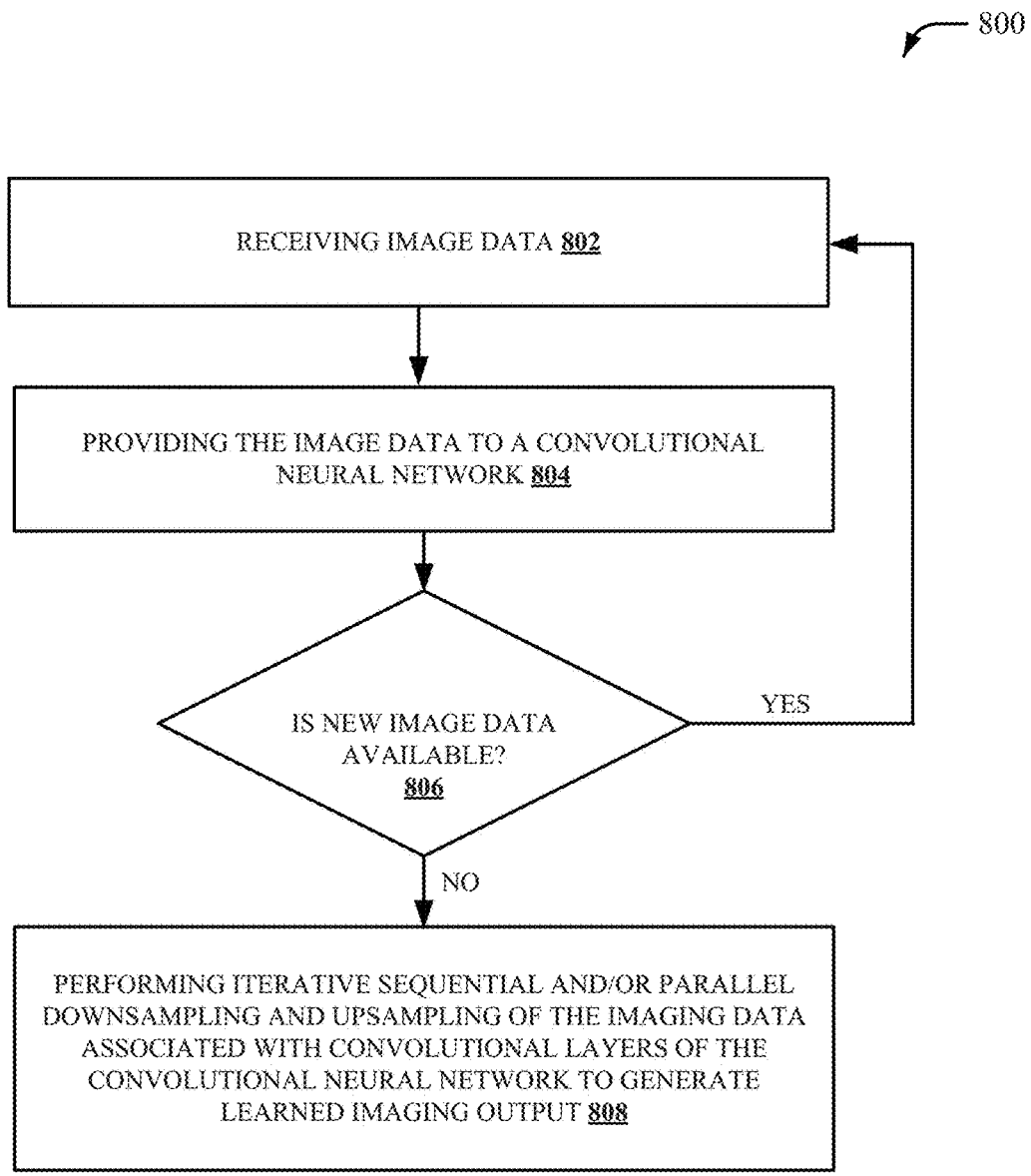
FIG. 8 depicts a flow diagram of an example method for providing a deep learning architecture for automated image feature extraction, in accordance with various aspects and implementations described herein.

FIG. 8 illustrates a methodology and/or a flow diagram in accordance with the disclosed subject matter. For simplicity of explanation, the methodology is depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodology in accordance with the disclosed subject matter. In addition, those skilled in the art will understand and appreciate that the methodology could alternatively be represented as a series of interrelated states via a state diagram or events. Additionally, it should be further appreciated that methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or storage media.

Referring to FIG. 8, there is illustrated a non-limiting implementation of a methodology 800 for providing a deep learning architecture for automated image feature extraction, according to an aspect of the subject innovation. At 802, image data is received (e.g., by machine learning component 104). The imaging data can be two-dimensional imaging data and/or three-dimensional imaging data generated by one or more imaging devices. For instance, the imaging data can be imagery captured via a set of sensors (e.g., a set of sensors associated with an imaging device). In certain embodiments, the imaging data can be a series of imagery captured via a set of sensors (e.g., a set of sensors associated with an imaging device) during an interval of time. The imaging data can be received directly from one or more imaging devices. Alternatively, the imaging data can be stored in one or more databases that receives and/or stores the imaging data associated with the one or more imaging devices. In certain embodiments, the image data can be medical imaging data. For example, the image data can be two-dimensional medical imaging data and/or three-dimensional medical imaging data generated by one or more medical imaging devices. In example, the image data can be electromagnetic radiation imagery captured via a set of sensors (e.g., a set of sensors associated with a medical imaging device). In certain embodiments, the image data can be a series of electromagnetic radiation imagery captured via a set of sensors (e.g., a set of sensors associated with a medical imaging device) during an interval of time. In another example, the image data can be positron emission tomography PET scan imagery. In yet another example, the image data can be magnetic resonance imaging MRI data. The image data can be received directly from one or more medical imaging devices. Alternatively, the image data can be stored in one or more databases that receives and/or stores the medical imaging data associated with the one or more medical imaging devices. A medical imaging device can be, for example, an x-ray device, a computed tomography CT device, a PET scanner device, an MRI device, another type of medical imaging device, etc.

At 804, the image data is provided (e.g., by machine learning component 104) to a convolutional neural network. The convolutional neural network can include, for example, one or more spring blocks associated with a deep learning architecture. The one or more spring blocks can be associated with sequential and/or parallel upsampling and downsampling. In an aspect, the one or more spring blocks can consist of one or more connected pair down sampling/up sampling layers and/or convolutional layers. The one or more spring blocks can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.).

At 806, it is determined whether new image data is available. If yes, methodology 800 returns to 802. If no, methodology 800 proceeds to 808.

At 808, iterative sequential and/or parallel downsampling and upsampling of the imaging data associated with convolutional layers of a convolutional neural network are performed (e.g., by machine learning component 104) to generate learned imaging output. In an embodiment, the performing the iterative sequential and/or parallel downsampling and upsampling of the imaging data can include analyzing the imaging data based on a first convolutional layer process that comprises a first depth and a second convolutional layer process that comprises a second depth. The first convolutional layer process can include first filter sizes and the second convolutional layer process can include second filter sizes that are different than the first filter sizes. In another embodiment, the performing the iterative sequential and/or parallel downsampling and upsampling of the imaging data can include performing the first convolutional layer process and the second convolutional layer process sequentially. In yet another embodiment, the performing the iterative sequential and/or parallel downsampling and upsampling of the imaging data can include performing the first convolutional layer process and the second convolutional layer process in parallel.

In certain embodiments, the methodology 800 can additionally or alternatively include classifying a feature for the imaging data based on the learned imaging output associated with the convolutional neural network. Additionally, in certain embodiments, the methodology 800 can additionally or alternatively include generating a multi-dimensional visualization associated with the classifying of the feature for the imaging data. In certain embodiments, the methodology 800 can additionally or alternatively include training a convolutional neural network by performing iterative sequential and/or parallel downsampling and upsampling of the imaging data associated with convolutional layers of the convolutional neural network. The training can include performing a first convolutional layer process that comprises a first depth and a second convolutional layer process that comprises a second depth. Additionally or alternatively, the first convolutional layer process can include first filter sizes and the second convolutional layer process can include second filter sizes that are different than the first filter sizes. Additionally or alternatively, the training can include performing the first convolutional layer process and the second convolutional layer process sequentially. Additionally or alternatively, the training can include performing the first convolutional layer process and the second convolutional layer process in parallel. In certain embodiments, the methodology 800 can additionally or alternatively include generating a set of filter values for the convolutional neural network based on the iterative sequential and/or parallel downsampling and upsampling of the imaging data.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 9:
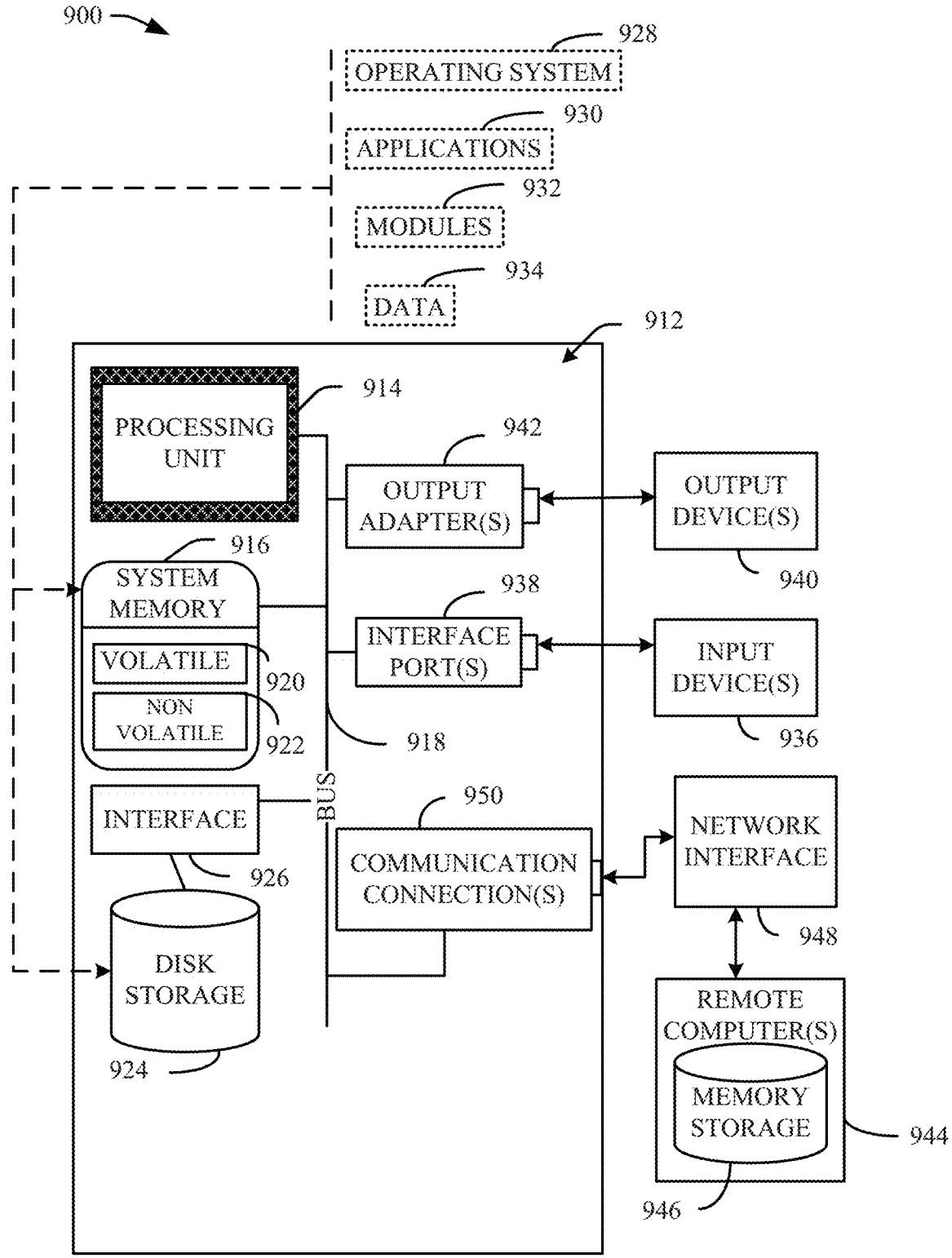
FIG. 9 is a schematic block diagram illustrating a suitable operating environment.
Figure 10:
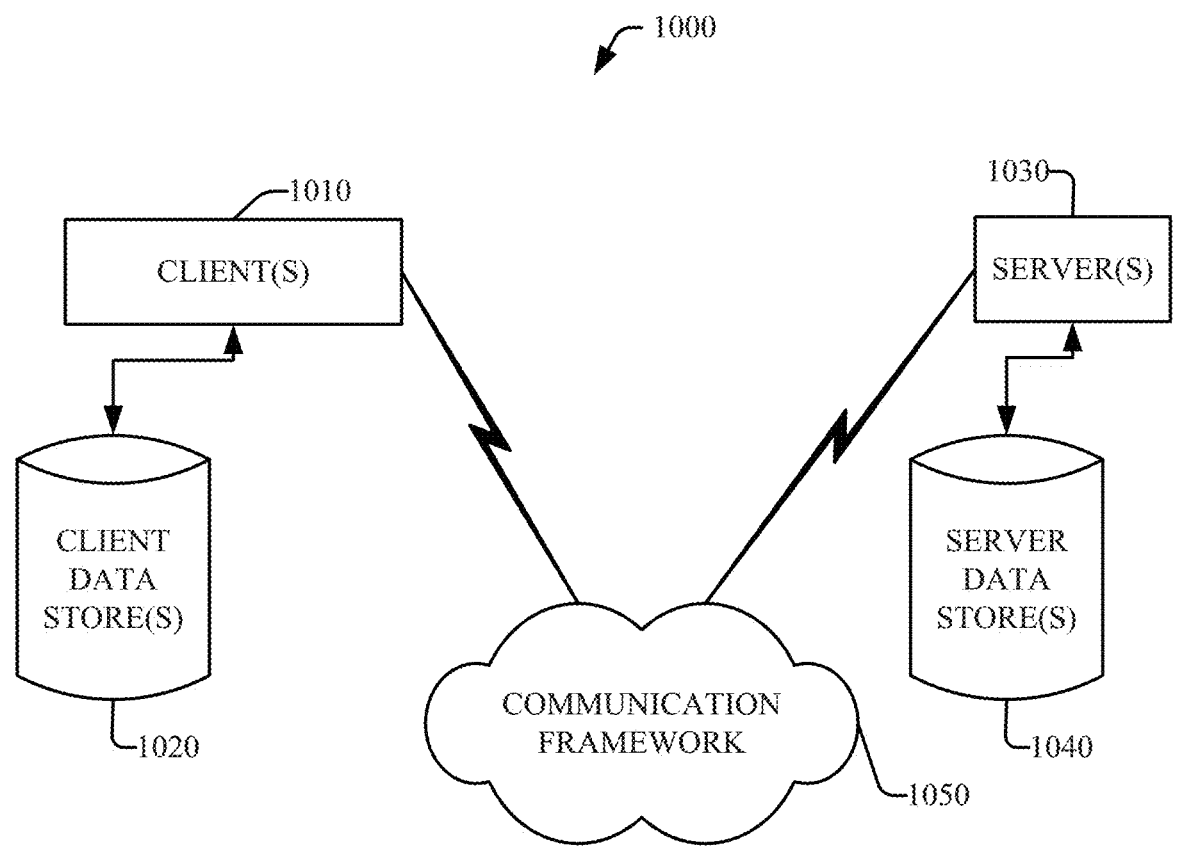
FIG. 10 is a schematic block diagram of a sample-computing environment.

In order to provide a context for the various aspects of the disclosed subject matter, FIGS. 9 and 10 as well as the following discussion are intended to provide a brief, general description of a suitable environment in which the various aspects of the disclosed subject matter may be implemented.

With reference to FIG. 9, a suitable environment 900 for implementing various aspects of this disclosure includes a computer 912. The computer 912 includes a processing unit 914, a system memory 916, and a system bus 918. The system bus 918 couples system components including, but not limited to, the system memory 916 to the processing unit 914. The processing unit 914 can be any of various available processors. Dual microprocessors and other multiprocessor architectures also can be employed as the processing unit 914.

The system bus 918 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 916 includes volatile memory 920 and nonvolatile memory 922. The basic input/output system (BIOS), containing the basic routines to transfer information between elements within the computer 912, such as during start-up, is stored in nonvolatile memory 922. By way of illustration, and not limitation, nonvolatile memory 922 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 920 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 912 also includes removable/non-removable, volatile/non-volatile computer storage media. FIG. 9 illustrates, for example, a disk storage 924. Disk storage 924 includes, but is not limited to, devices like a magnetic disk drive, floppy disk drive, tape drive, Jaz drive, Zip drive, LS-100 drive, flash memory card, or memory stick. The disk storage 924 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 924 to the system bus 918, a removable or non-removable interface is typically used, such as interface 926.

FIG. 9 also depicts software that acts as an intermediary between users and the basic computer resources described in the suitable operating environment 900. Such software includes, for example, an operating system 928. Operating system 928, which can be stored on disk storage 924, acts to control and allocate resources of the computer system 912. System applications 930 take advantage of the management of resources by operating system 928 through program modules 932 and program data 934, e.g., stored either in system memory 916 or on disk storage 924. It is to be appreciated that this disclosure can be implemented with various operating systems or combinations of operating systems.

A user enters commands or information into the computer 912 through input device(s) 936. Input devices 936 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 914 through the system bus 918 via interface port(s) 938. Interface port(s) 938 include, for example, a serial port, a parallel port, a game port, and a universal serial bus (USB). Output device(s) 940 use some of the same type of ports as input device(s) 936. Thus, for example, a USB port may be used to provide input to computer 912, and to output information from computer 912 to an output device 940. Output adapter 942 is provided to illustrate that there are some output devices 940 like monitors, speakers, and printers, among other output devices 940, which require special adapters. The output adapters 942 include, by way of illustration and not limitation, video and sound cards that provide a means of connection between the output device 940 and the system bus 918. It should be noted that other devices and/or systems of devices provide both input and output capabilities such as remote computer(s) 944.

Computer 912 can operate in a networked environment using logical connections to one or more remote computers, such as remote computer(s) 944. The remote computer(s) 944 can be a personal computer, a server, a router, a network PC, a workstation, a microprocessor based appliance, a peer device or other common network node and the like, and typically includes many or all of the elements described relative to computer 912. For purposes of brevity, only a memory storage device 946 is illustrated with remote computer(s) 944. Remote computer(s) 944 is logically connected to computer 912 through a network interface 948 and then physically connected via communication connection 950. Network interface 948 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 950 refers to the hardware/software employed to connect the network interface 948 to the bus 918. While communication connection 950 is shown for illustrative clarity inside computer 912, it can also be external to computer 912. The hardware/software necessary for connection to the network interface 948 includes, for exemplary purposes only, internal and external technologies such as, modems including regular telephone grade modems, cable modems and DSL modems, ISDN adapters, and Ethernet cards.

FIG. 10 is a schematic block diagram of a sample-computing environment 1000 with which the subject matter of this disclosure can interact. The system 1000 includes one or more client(s) 1010. The client(s) 1010 can be hardware and/or software (e.g., threads, processes, computing devices). The system 1000 also includes one or more server(s) 1030. Thus, system 1000 can correspond to a two-tier client server model or a multi-tier model (e.g., client, middle tier server, data server), amongst other models. The server(s) 1030 can also be hardware and/or software (e.g., threads, processes, computing devices). The servers 1030 can house threads to perform transformations by employing this disclosure, for example. One possible communication between a client 1010 and a server 1030 may be in the form of a data packet transmitted between two or more computer processes.

The system 1000 includes a communication framework 1050 that can be employed to facilitate communications between the client(s) 1010 and the server(s) 1030. The client(s) 1010 are operatively connected to one or more client data store(s) 1020 that can be employed to store information local to the client(s) 1010. Similarly, the server(s) 1030 are operatively connected to one or more server data store(s) 1040 that can be employed to store information local to the servers 1030.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A convolutional neural network system, comprising:
   a memory that stores computer executable components;
   a processor that executes computer executable components stored in the memory, wherein the computer executable components comprise:
     a machine learning component that generates learned imaging output regarding imaging data based on a convolutional neural network that receives the imaging data, wherein the convolutional neural network comprises a plurality of sequential spring blocks in series with a plurality of parallel spring blocks, wherein a spring block comprises a sequence of downsampling layers in series with a corresponding sequence of upsampling layers.

2. The convolutional neural network system of claim 1, wherein the machine learning component analyzes the imaging data based on a first spring block that comprises a first depth and a second spring block that comprises a second depth that is different from the first depth.

3. The convolutional neural network system of claim 2, wherein the first spring block comprises first filter sizes and the second spring block comprises second filter sizes that are different than the first filter sizes.

4. The convolutional neural network system of claim 2, wherein the machine learning component executes the first spring block and the second spring block sequentially.

5. The convolutional neural network system of claim 2, wherein the machine learning component executes the first spring block and the second spring block in parallel.

6. The convolutional neural network system of claim 1, wherein the machine learning component determines a classification and an associated localization for a portion of the imaging data based on the learned imaging output associated with the convolutional neural network.

7. The convolutional neural network system of claim 6, wherein the computer executable components further comprise:
   a visualization component that generates a multi-dimensional visualization associated with the classification and the localization for the portion of the imaging data.

8. A method, comprising:
   receiving, by a system comprising a processor, imaging data; and
   generating, by the system, learned imaging output by analyzing the imaging data with a convolutional neural network, wherein the convolutional neural network comprises a plurality of sequential spring blocks in series with a plurality of parallel spring blocks, wherein a spring block comprises a sequence of downsampling layers in series with a corresponding sequence of upsampling layers.

9. The method of claim 8, wherein the generating the learned imaging output comprises analyzing the imaging data based on a first spring block that comprises a first depth and a second spring block that comprises a second depth that is different from the first depth.

10. The method of claim 9, wherein the first spring block comprises first filter sizes and the second spring block comprises second filter sizes that are different than the first filter sizes.

11. The method of claim 9, wherein the generating the learned imaging output comprises executing the first spring block and the second spring block sequentially.

12. The method of claim 9, wherein the generating the learned imaging output comprises executing the first spring block and the second spring block in parallel.

13. The method of claim 8, wherein the method further comprises:

classifying, by the system, a feature for the imaging data based on the learned imaging output associated with the convolutional neural network.

14. The method of claim 13, wherein the method further comprises:

generating, by the system, a multi-dimensional visualization associated with the classifying of the feature for the imaging data.

15. A method, comprising:

receiving, by a system comprising a processor, imaging data that comprises a set of images; and training, by the system, a convolutional neural network, wherein the convolutional neural network comprises a plurality of sequential spring blocks in series with a plurality of parallel spring blocks, wherein a spring block comprises a sequence of downsampling layers in series with a corresponding sequence of upsampling layers.

16. The method of claim 15, wherein the training comprises executing a first spring block that comprises a first depth and a second spring block that comprises a second depth that is different from the first depth.

17. The method of claim 16, wherein the first spring block comprises first filter sizes and the second spring block comprises second filter sizes that are different than the first filter sizes.

18. The method of claim 16, wherein the training comprises executing the first spring block and the second spring block sequentially.

19. The method of claim 16, wherein the training comprises executing the first spring block and the second spring block in parallel.

20. The method of claim 13, wherein the method further comprises:

generating, by the system, a set of filter values for the convolutional neural network based on iterative sequential or parallel downsampling and upsampling of the imaging data.

* * * * *